United States Patent
Kelly

(10) Patent No.: US 10,532,175 B1
(45) Date of Patent: Jan. 14, 2020

(54) METHODS FOR MINIMIZING DELAYED EFFECTS OF EXPOSURE TO REDUCED OXYGEN PARTIAL PRESSURE VIA ADMINISTRATION OF SUPPLEMENTAL OXYGEN

(71) Applicant: Model Software Corporation, New Orleans, LA (US)

(72) Inventor: John J. Kelly, New Orleans, LA (US)

(73) Assignee: MODEL SOFTWARE CORPORATION, New Orleans, LA (US)

( * ) Notice: Subject to any disclaimer, the term of this patent is extended or adjusted under 35 U.S.C. 154(b) by 0 days.

(21) Appl. No.: 16/420,709

(22) Filed: May 23, 2019

Related U.S. Application Data

(63) Continuation of application No. 15/864,625, filed on Jan. 8, 2018, now abandoned, which is a continuation
(Continued)

(51) Int. Cl.
*A61M 16/00* (2006.01)
*A62B 7/14* (2006.01)
*A61M 16/10* (2006.01)

(52) U.S. Cl.
CPC ....... *A61M 16/1005* (2014.02); *A61M 16/101* (2014.02); *A61M 2016/1025* (2013.01);
(Continued)

(58) Field of Classification Search
CPC ............ A61M 16/1005; A61M 16/101; A61M 2016/102; A61M 2016/1025;
(Continued)

(56) References Cited

U.S. PATENT DOCUMENTS 3,672,384 A * 6/1972 Hellquist ............... A62B 9/022
137/39
4,198,213 A 4/1980 Mannatt
(Continued)

FOREIGN PATENT DOCUMENTS

EP 0808769 A2 11/1997

OTHER PUBLICATIONS

"FAA, "Section I, 1.2—Space"", Available online at<https://www.faa.gov/about/office_org/headquarters_offices/ays/offices/aam/cami/library/online_libraries/aerospace_medicine/tutorial/media/1.1.2_Space.doc>.
(Continued)

*Primary Examiner* — Joseph D. Boecker
(74) *Attorney, Agent, or Firm* — Buchanan Ingersoll & Rooney PC

(57) ABSTRACT

Described herein are methods which involve minimizing or eliminating the occurrence of delayed negative effects that may arise from exposure to reduced oxygen partial pressure. An amount of supplemental oxygen, which substantially mimics a target oxygen partial pressure, is administered to an individual that is exposed to a reduced oxygen partial pressure environment, to compensate for the reduced oxygen partial pressure. The target partial pressure may be selected such that the individual experiences substantially no change in the oxygen partial pressure. Individuals receiving the supplemental oxygen may be healthy, have special sensitivities, or have a pre-existing neurological condition.

16 Claims, 2 Drawing Sheets

Related U.S. Application Data of application No. 15/403,240, filed on Jan. 11, 2017, now abandoned.

(52) U.S. Cl.
CPC ............... *A61M 2202/0208* (2013.01); *A61M 2205/3334* (2013.01); *A62B 7/14* (2013.01)

(58) Field of Classification Search
CPC .... A61M 2202/0208; A61M 2230/205; A62B 7/02; A62B 7/14; A62B 11/00; B64D 2013/0681; B64D 2231/00; B64D 2231/02; B64D 2231/025
See application file for complete search history.

(56) References Cited

U.S. PATENT DOCUMENTS

| | | | |
|---|---|---|---|
| 4,210,137 | A | 7/1980 | Henkin |
| 4,651,728 | A | 3/1987 | Gupta et al. |
| 5,247,926 | A | 9/1993 | Harral |
| 5,357,949 | A | 10/1994 | Bertheau et al. |
| 5,590,852 | A | 1/1997 | Olson |
| 5,791,982 | A | 8/1998 | Curry et al. |
| 5,809,999 | A | 9/1998 | Lang |
| 6,244,540 | B1 | 6/2001 | Stabile et al. |
| 6,302,106 | B1 | 10/2001 | Lewis |
| 6,382,563 | B1 | 5/2002 | Chiu |
| 6,669,758 | B1 | 12/2003 | Hart et al. |
| 6,923,183 | B2 | 8/2005 | Martinez et al. |
| 7,040,319 | B1 | 5/2006 | Kelly et al. |
| 7,082,946 | B2 | 8/2006 | Farin et al. |
| 7,246,620 | B2 | 7/2007 | Conroy, Jr. |
| 7,331,343 | B2 * | 2/2008 | Schmidt ............... A61M 16/026 128/204.18 |
| 8,052,087 | B2 | 11/2011 | Jörn |
| 8,474,456 | B2 | 7/2013 | Rittner et al. |
| 8,689,790 | B2 | 4/2014 | Cannon |
| 8,795,041 | B2 | 8/2014 | Saito et al. |
| 9,022,033 | B2 | 5/2015 | Hk |
| 9,345,913 | B2 | 5/2016 | Rittner et al. |
| 2002/0096174 | A1 | 7/2002 | Hill et al. |
| 2002/0139368 | A1 | 10/2002 | Bachinski |
| 2004/0206353 | A1 | 10/2004 | Conroy |
| 2005/0126570 | A1 | 6/2005 | Phillips |
| 2006/0068693 | A1 | 3/2006 | Kono et al. |
| 2006/0201504 | A1 | 9/2006 | Singhal et al. |
| 2007/0089746 | A1 | 4/2007 | Mitchell et al. |
| 2009/0044800 | A1 * | 2/2009 | Jorn ............... A62B 7/14 128/203.12 |
| 2009/0165796 | A1 | 7/2009 | Aubonnet et al. |
| 2009/0301489 | A1 | 12/2009 | Bloch et al. |
| 2010/0043788 | A1 | 2/2010 | Fine et al. |
| 2010/0043794 | A1 | 2/2010 | Saito et al. |
| 2010/0258127 | A1 * | 10/2010 | HK ............... A62B 7/14 128/205.11 |
| 2011/0240017 | A1 * | 10/2011 | Butler ............... A61G 10/04 128/201.25 |
| 2011/0290250 | A1 | 12/2011 | Olson et al. |
| 2012/0118285 | A1 | 5/2012 | Wondka et al. |
| 2013/0247913 | A1 | 9/2013 | Aubonnet et al. |
| 2013/0312745 | A1 | 11/2013 | Kshirsagar et al. |
| 2014/0123980 | A1 | 5/2014 | Rissacher et al. |
| 2014/0318989 | A1 | 10/2014 | Dhas |
| 2014/0366875 | A1 * | 12/2014 | Motlagh ............... A62B 7/02 128/202.26 |
| 2015/0157883 | A1 | 6/2015 | Armatorio et al. |
| 2015/0157884 | A1 | 6/2015 | Armatorio et al. |
| 2015/0174359 | A1 * | 6/2015 | Elliott ............... A61M 16/1005 128/204.22 |
| 2015/0196245 | A1 | 7/2015 | Peake |
| 2016/0026188 | A1 | 1/2016 | Lanterna et al. |

OTHER PUBLICATIONS

"Section I, 1.2—Space", FAA, retrieved from https://www.faa.gov/about/office_org/headquarters_offices/ays/offices/aam/cami/library/online_libraries/aerospace_medicine/tutorial/media/1.1.2_pace.doc.

"State-of-the-art medical equipment", Swiss Air-Ambulance, retrieved from https://web.archive.org/web/20150325132719/https://www.rega.ch/en/swiss-air-ambulance/medical-equipment.aspx with date.

"Swiss Air-Ambulance, "State-of-the-art medical equipment"", Available online at<https://web.archive.org/web/20150325132719/https://www.rega.ch/en/swiss-air-ambulance/medical-equipment.aspx with date>, Mar. 25, 2015.

England, Harvey M, et al., "Comparisons of Molecular Sieve Oxygen Concentrators for Potential Medical Use Aboard Commercial Aircraft", , Jun. 1992, pp. I-7.

England, Jr., Harvey M., et al., "Comparisons of Molecular Sieve Oxygen Concentrators for Potential Medical Use Aboard Commercial Aircraft", DOT/FAA/AM-92/22, Jun. 1992, pp. 1-7.

FAA, "Section 1, 1.2—Space", https://www.faa.gov/about/office_org/headquarters_offices/avs/offices/aam/cami/library/online_libraries/aerospace_medicine/tutorial/media/I.1.2_Space.doc.

Franzen, et al., "Le patient comme passager aerien", 698-704.

Franzen, et al., "Le patient comme passager aerien", Forum Med Suisse, vol. 8, No. 38, translation submitted , 2008, pp. 698-704.

Huff, Anndee L, et al., "Sustainable Oxygen: A Low Power Approach for Providing Emergency Medical Oxygen for Spacecraft and Hospitals in Developing Countries", Jul. 1, 2011, pp. I-9.

Huff, Anndee L., et al., "Sustainable Oxygen: A Low Power Approach for Providing Emergency Medical Oxygen for Spacecraft and Hospitals in Developing Countries", Portland State University, PDX Scholar, Mechanical and Materials Engineering, Jul. 1, 2011, pp. 1-9.

PCT/US2017/068069, "Notification of Transmittal of the International Search Report and the Written Opinion Received", 11 pages.

Seidenberg, et al., "Future Neural", vol. 4, No. 5, Doi:10.2217/fnl. 09.32, Sep. 1, 2009.

Seidenberg, et al. , "Future Neurol", Doi:10.2217/fnl.09.32. vol. 4(5):, Sep. 1, 2009, pp. 663-668.

Seidenberg, et al., "Future Neurol. Sep. 2009", 663-668.

Swiss Air-Ambulance, "State-of-the-art medical equipment", https://web.archive.org/web/20150325132719/https://www.rega.ch/en/swiss-air-ambulance/medical-equipment.aspx , Mar. 25, 2015.

Translation of Franzen, et al., "Le patient comme passager aerien".

Trevorrow, Tracy, "Air Travel and Seizure Frequency for Individuals With Epilepsy", Seizure, vol. 15, pp. 320-327.

Trevorrow, Tracy, "IR Travel and Seizure Frequency for Individuals With Epilepsy", 2006, pp. 320-327.

\* cited by examiner

METHODS FOR MINIMIZING DELAYED EFFECTS OF EXPOSURE TO REDUCED OXYGEN PARTIAL PRESSURE VIA ADMINISTRATION OF SUPPLEMENTAL OXYGEN

TECHNICAL FIELD

The present disclosure relates to methods for minimizing the delayed effects of exposure to reduced oxygen partial pressure on an individual, particularly by administering supplemental oxygen for a period of time to compensate for the reduced oxygen partial pressure existing in an environment.

BACKGROUND

Oxygen is critical to human life. Each cell, tissue, and function of the human body requires oxygen. Without oxygen, cells cannot function, repair, and restore. A shortage of oxygen, or hypoxia, can thus cause several problems, some of which carry immediately noticeable effects. Examples of symptoms of hypoxia may include, but are not limited to, nausea, headache, fatigue, and shortness of breath. In severe cases, hypoxia may result in loss of consciousness, seizures, coma, and even death.

High altitudes reduce the partial pressure of oxygen in the lungs. Exposure to a reduced oxygen partial pressure environment, such as in a pressurized aircraft, can thus result in hypoxia. The pressure in an aircraft cabin at altitude is typically maintained at the pressure one would experience at about 7,000 feet (approximately 11 psi). A similar effect is observed in geographic locations at high altitudes. For example, the partial pressure of oxygen is reduced for a high altitude city, such as Denver, Colo., when compared to the partial pressure of oxygen of a city at sea level, such as New Orleans, La. The "station pressure" in Denver is typically about 23-24 inches/hg (about 12 psi) versus the "station pressure" at sea level, which is typically around 30 inches/hg (about 15 psi).

Oxygen accounts for approximately 21% of dry air and the partial pressure of oxygen will decrease in proportion to the decrease in ambient pressure. Accordingly, and by way of example, the partial pressure of oxygen in ambient pressure at sea level is approximately 3.1 psi and will thus proportionally decrease to approximately 2.3 psi in the pressurized aircraft cabin.

A person's sensitivity to reduced oxygen partial pressure environments and/or high altitudes can generally be classified into one of two categories—normal healthy persons and persons having special sensitivities. A normal healthy person will typically not experience side effects from exposure to reduced oxygen partial pressure, such as that observed during air transport on an aircraft at altitude or at a geographic location having a high altitude. A small subset of healthy persons, however, will experience some side effects from exposure to reduced oxygen partial pressure environment, such as that observed during air transport on an aircraft at altitude. This may typically be described as "feeling lousy" after a flight. The other category of individuals includes those with special sensitivities. These persons are individuals who more often than not have pre-existing neurological conditions, such as epilepsy. These persons may or may not experience immediate episodes or symptoms from being at a high altitude, but may instead be susceptible to delayed effects that present following a period of exposure to a reduced oxygen partial pressure environment. One example is that persons with certain forms of epilepsy may not experience symptoms or episodes while exposed to a reduced oxygen partial pressure environment, but instead may have an increased risk of experiencing seizures in a relatively short period of time, up to a few days, following the exposure.

Presently, there are a number of techniques to treat the contemporaneous effects of oxygen deprivation observed from exposure to a reduced oxygen partial pressure environment. One such well-known technique is the administration of supplemental oxygen. When an individual becomes hypoxic after suffering some degree of oxygen deprivation, supplemental oxygen is then supplied to compensate for the observed oxygen deprivation. However, this technique is only applied to address the contemporaneous or immediate effects resulting from the oxygen deprivation. It is not used preventatively to minimize or eliminate the delayed effects of exposure to reduced oxygen partial pressure.

Another similar, well-known technique is administering supplemental oxygen to relieve acute symptoms from exposure to a reduced oxygen partial pressure environment to facilitate/maintain pilot concentration at altitude. In this regard, it is known to provide aircraft pilots with supplemental oxygen to deter the occurrence of a loss of consciousness and/or concentration at high altitudes upon exposure to reduced oxygen partial pressure. Much like the above-mentioned methods for treating hypoxia, supplemental oxygen is provided to abate the immediate effects of oxygen deprivation.

Supplemental oxygen administration also has known applications in treating persons having pre-existing pulmonary conditions. Similar to the treatment of hypoxia, the use of supplemental oxygen for persons having pre-existing pulmonary conditions is therapeutic in nature and contemporaneous to the known condition.

Known oxygen delivery devices are operable to supply oxygen to a person according to one of two ways—at a fixed flow rate or on demand. When oxygen is supplied at a fixed flow rate, the oxygen is typically delivered at a set volume and a set flow rate, regardless of the individual's need for oxygen. This is true when the individual's demand for oxygen is either higher or lower than the amount of oxygen delivered by the set flow rate. In an on demand delivery device, oxygen is supplied to the individual during an inhalation cycle. On demand delivery devices tend to conserve more oxygen than the constant flow rate devices since oxygen is only supplied when the individual inhales rather than continuously free flowing throughout the individual's respiration cycle.

Supplying oxygen also requires controlling the flow rate to meet an individual's demand. This can be effectuated according to any of the several techniques for estimating demand known to those of skill in the art. In some techniques, one or more pressure sensors are placed in relative proximity to an individual's breathing location (e.g., nose or mouth) to measure the ambient pressure and the individual's breathing pressure. The breathing pressure represents the air inhaled and/or exhaled by the individual during a respiration cycle. The measured pressure values are then used to regulate the flow rate. It is common practice for the flow rate to be adjusted such that the pressure differential between the ambient pressure and the breathing pressure is zero. Other exemplary methods for estimating the demand for oxygen involve measuring the amount of carbon dioxide exhausted by the person, measuring the rate of breathing, measuring the flow rate, and measuring the level of activity of a person.

It is also known to control the demand for oxygen by varying the concentration of the oxygen being administered. This is typically effectuated by providing a supply of ambient air mixed with pure oxygen. Since the concentration of oxygen decreases as altitude increases, compensation for this differential can be achieved by increasing the proportion of pure oxygen administered to an individual for a higher altitude.

As indicated above, there are several known techniques for treating the immediate effects of oxygen deprivation. But, these techniques do not consider the negative effects that may occur subsequent to exposure to a reduced oxygen partial pressure environment. Accordingly, there exists a need to develop a preventative measure or technique to compensate for an exposure to a reduced oxygen partial pressure environment in order to minimize or eliminate the occurrence of delayed effects from the exposure, specifically in persons having special sensitivities.

SUMMARY

The present disclosure provides a description of methods for minimizing the delayed effects on an individual resulting from exposure to reduced oxygen partial pressure via the administration of supplemental oxygen. The present disclosure also relates to a post-flight seizure prevention method.

In one embodiment, a method for minimizing delayed effects of exposure to a reduced oxygen partial pressure involves providing a source of supplemental oxygen. Because reduced oxygen partial pressure is known to occur on flights at altitude, the source of supplemental oxygen should be suitable for transport on an aircraft during a flight at altitude. The supplemental oxygen is administered to a person during air transport on the aircraft to compensate for the reduced oxygen partial pressure that exists in the aircraft during the flight. Further, the supplemental oxygen is administered to maintain a target oxygen partial pressure for a period of time such that the person receiving the supplemental oxygen experiences substantially no change in the oxygen partial pressure. The target oxygen partial pressure is an oxygen partial pressure to which the person receiving the supplemental oxygen is routinely accustomed or acclimatized.

In another embodiment, a method for minimizing delayed effects of exposure to a reduced oxygen partial pressure involves providing a portable source of supplemental oxygen. An amount of supplemental oxygen that closely mimics a target oxygen partial pressure is administered to an individual presently exposed to a reduced oxygen partial pressure. The supplemental oxygen is administered to maintain a target oxygen partial pressure for a period of time such that the person receiving the supplemental oxygen experiences little to no change in the oxygen partial pressure. The target oxygen partial pressure is an oxygen partial pressure to which the person receiving the supplemental oxygen is routinely accustomed or acclimatized.

In yet another embodiment, there is disclosed a post-flight seizure prevention method. The post-flight seizure prevention method involves providing a portable source of supplemental oxygen suitable for transport on an aircraft during a flight at altitude and administering the supplemental oxygen to a person during air transport on the aircraft to compensate for a reduced oxygen partial pressure existing in the aircraft during the flight. The supplemental oxygen is administered in an amount such that the person receiving the supplemental oxygen experiences an oxygen partial pressure that substantially mimics a target oxygen partial pressure. In some instances, the target oxygen partial pressure is an oxygen partial pressure to which the person receiving the supplemental oxygen is routinely accustomed or acclimatized.

DESCRIPTION OF DRAWING FIGURES

DETAILED DESCRIPTION

Figure 1:
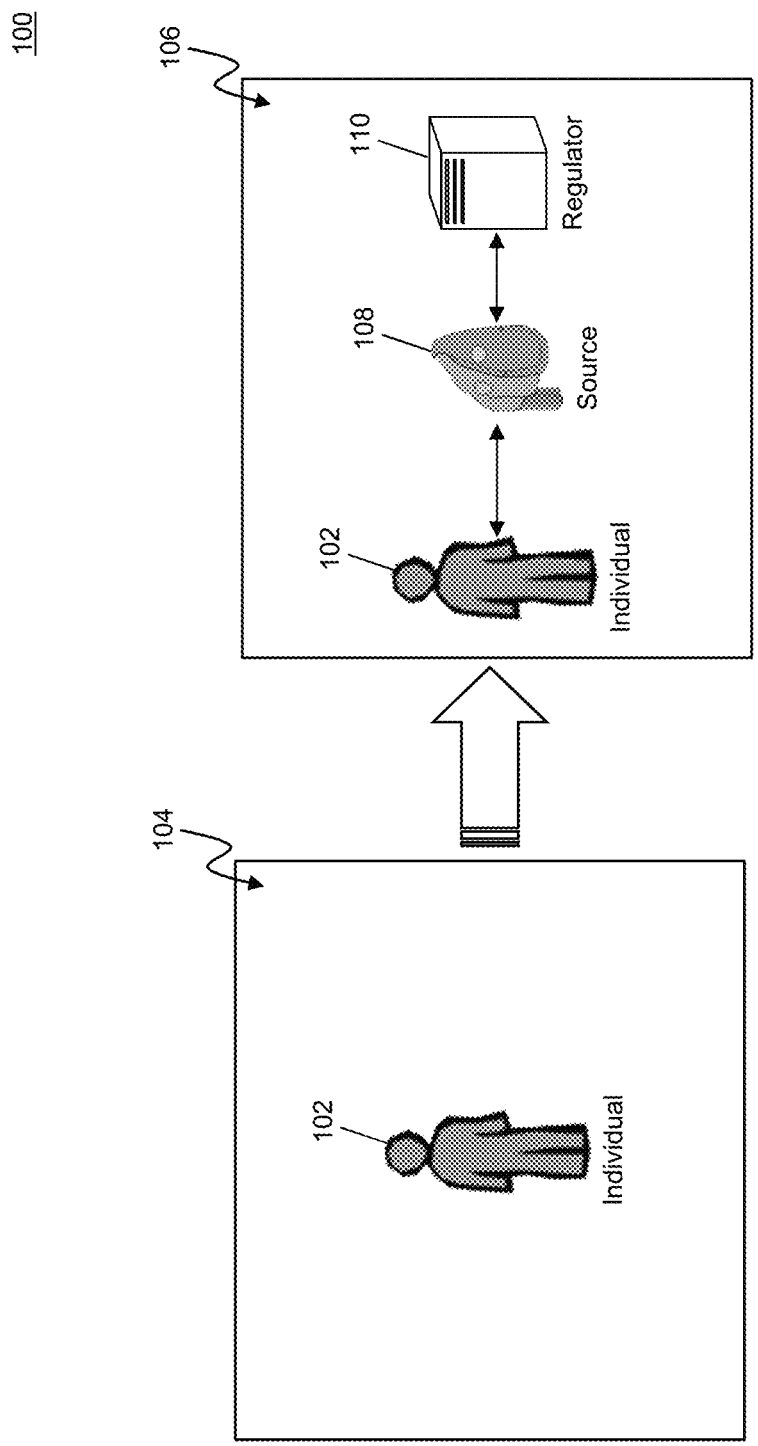
FIG. 1 is a block diagram illustrating a system for providing a source of supplemental oxygen to minimize delayed effects of exposure to a reduced oxygen partial pressure in accordance with exemplary embodiments.

The methods presented herein seek to address the delayed effects that may arise from an individual's exposure to a reduced oxygen partial pressure environment. These methods are preventative in nature and involve steps to compensate in real-time for the reduced oxygen partial pressure environment to either minimize or eliminate the negative physiological effects that can result from exposure to reduced oxygen partial pressure.

In one embodiment, the delayed effects resulting from exposure to a reduced oxygen partial pressure 106 are mitigated by administering an amount of supplemental oxygen to an individual 102. The source 108 of the supplemental oxygen is not limited to any particular device, but in some embodiments it is preferable that the source be portable. The portability of the supplemental oxygen will afford the individual 102 receiving the supplemental oxygen some level of mobility. In other embodiments, it is preferable that the source 108 of the supplemental oxygen is not separately portable, but is instead mounted to or installed directly within a transportation vehicle. For example, the source 108 of supplemental oxygen may be built-in to the cabin of an aircraft, such that the supplemental oxygen is deliverable to individual seats or sections of the aircraft. It is also contemplated that the transportation vehicles are not limited solely to aircraft vehicles. Such vehicles may include any of those which traverse or encounter a reduced oxygen partial pressure environment.

The amount of supplemental oxygen that is supplied to the individual 102 exposed to the reduced oxygen partial pressure environment 106 is set to provide a target oxygen partial pressure. Ideally, the target oxygen partial pressure is set to mimic the typical oxygen partial pressure environment 104 to which the individual 102 is normally accustomed. The typical oxygen partial pressure environment 104 to which the individual 102 is normally accustomed may also be understood to be the individual's home oxygen partial pressure. For the purposes of this disclosure, the oxygen partial pressure to which the individual 102 is normally accustomed and home oxygen partial pressure may be used interchangeably.

For example, if the individual 102 spends most of his/her time at sea level, the target oxygen partial pressure would be set to be the same as the oxygen partial pressure at sea level (approximately 3 psi). In other words, the home oxygen partial pressure would be 3 psi. The target partial pressure is set in this manner such that the individual 102 receiving the supplemental oxygen ideally experiences a zero net differential oxygen partial pressure between the reduced oxygen partial pressure environment 106 to which he/she is presently exposed and the home oxygen partial pressure environment 102. Regulating, by a regulator 110, the target oxygen partial pressure such that there is a zero net differential oxygen partial pressure with respect to the reduced oxygen partial pressure environment 106 essentially has the effect of negating any impact the reduced oxygen partial pressure environment 106 exerts on the individual 102. Even though the individual 102 is exposed to a reduced oxygen partial pressure environment 106, the individual 102 experiences substantially no change in oxygen partial pressure from his/her home oxygen partial pressure environment 104.

The ideal scenario is one in which an individual 102 experiences a zero net differential oxygen partial pressure. It is not unforeseeable that a zero net differential oxygen partial pressure may not be obtainable. It may not be possible to obtain a zero net differential oxygen partial pressure for some portion of time during the course of the administration of the supplemental oxygen. It may also not be possible to achieve a zero net differential oxygen partial pressure at any point during the duration of the supplemental oxygen administration. However, the methods described herein may be used to minimize the net differential oxygen partial pressure to some extent. It is contemplated that any level of minimization of the net differential oxygen partial pressure between the reduced oxygen partial pressure environment 106 to which an individual 102 is presently exposed and the home oxygen partial pressure 104 using the methods described herein is preferable to no offset.

It is further contemplated that a surplus of supplemental oxygen may be supplied to an individual 102 using any of the methods described herein. A surplus of supplemental oxygen may be understood as a supply of pure oxygen. Supplying pure oxygen to an individual 102 to compensate for exposure to a reduced oxygen partial pressure environment is acceptable within the metes and bounds of the methods discussed here provided that the pure oxygen is administered short term. Short term administration may be understood as a period of time up to and including a number of hours. For example, pure oxygen may be supplied for a period not to exceed 24 hours (or one day). An upper limit of the specific number of hours may vary by individual 102, but pure oxygen should not be administered for a long enough duration to trigger negative effects in the individual receiving the oxygen.

The target oxygen partial pressure may also be an oxygen partial pressure that is not the person's home oxygen partial pressure. Instead, the target oxygen partial pressure may be set to be an oxygen partial pressure to which the person 102 is presently or temporarily acclimatized. For example, an individual's home oxygen partial pressure may be the oxygen partial pressure at sea level (approximately 3 psi), while the individual's acclimatized partial pressure is the oxygen partial pressure at a higher altitude (e.g., 2.8 psi).

It is desirable that the target oxygen partial pressure is adjustable in the disclosed methods. In some embodiments, it is preferable for the target oxygen partial pressure to remain constant while in other embodiments it is preferable for the target oxygen partial pressure to vary over the course of the administration of the supplemental oxygen.

An initial target oxygen partial pressure may be set to the oxygen partial pressure to which the individual 102 receiving the supplemental oxygen is acclimatized. For example, the initial target oxygen partial pressure could be set to the oxygen partial pressure at sea level (approximately 3 psi). If, by way of example, the individual 102 is traveling to a location having a reduced oxygen partial pressure (e.g., higher altitude), it may be desirable to gradually compensate for the shift in oxygen partial pressure between locations. In this case, the higher altitude location could be said to have an end target oxygen partial pressure of approximately 2.6 psi. To compensate for the reduction in oxygen partial pressure from the initial location to the end destination, the target oxygen partial pressure may be gradually varied during the course of administration of supplemental oxygen from 3 psi to 2.6 psi. The change in target oxygen partial pressure can be effectuated either automatically or manually.

In another embodiment, the delayed effects resulting from exposure to a reduced oxygen partial pressure on an aircraft at altitude are mitigated by administering an amount of supplemental oxygen to an individual 102. The source 108 of the supplemental oxygen is not limited to any particular device, but should be approved for transport on an aircraft during a flight at altitude. One exemplary portable source 108 of supplemental oxygen is the Invacare® XPO2 Portable Oxygen Concentrator (Product ID: XPO100). In some embodiments, it is preferable that the source 108 of the supplemental oxygen is not separately portable, but is instead mounted to or installed directly within the aircraft. An amount of supplemental oxygen is administered to the individual 102 during air transport on the aircraft to compensate for the reduced oxygen pressure existing in the aircraft during the flight.

The amount of supplemental oxygen that is supplied to the individual 102 is set (e.g., via the regulator 110) to provide a target oxygen partial pressure. Similar to that discussed above, the target oxygen partial pressure can be constant or adjustable. Ideally, the target oxygen partial pressure is set such that the individual 102 receiving the supplemental oxygen experiences no change in the oxygen partial pressure from the departure airport to the arrival airport. Depending on the duration of the flight and/or the equipment, a zero net differential in oxygen partial pressure may not be obtainable. Compensation may only be available for a portion of the flight rather than its entirety. Regardless, some amount of compensation for the reduced oxygen partial pressure at altitude is preferable to no compensation.

Under-compensation or temporary overcompensation of the reduced oxygen partial pressure may occur. In either case, administration of supplemental oxygen, whether it undercompensates or overcompensates for the reduced oxygen partial pressure environment is preferable to providing no compensation whatsoever.

In some embodiments, it may be problematic to deliver a too high of a level of oxygen when administering supplemental oxygen. For example, a person 102 that is climbing a mountain or is otherwise exposed to a reduced oxygen partial pressure for a significant period of time (e.g., days, weeks, etc.) may not be able to receive pure oxygen as supplemental oxygen for the duration of their exposure. In such embodiments, the supplemental oxygen may be enriched to a selected concentration, such as one that is not pure (e.g., not 100%) oxygen. For instance, oxygen may be enriched with other air to supplement the individual 102 to achieve the ideal oxygen partial pressure while reducing the opportunity for overexposure to pure oxygen. In an example, a device 108 for delivering supplemental oxygen may include a first tube that delivers pure oxygen with a second tube that delivers ambient air, where the output of the tubes are mixed in a predetermined ratio to achieve the desired oxygen partial pressure. In such an example, the predetermined ratio may be varied via electric or manual modification to the flow rate of pumps for each tube (e.g., via the regulator 110), varying of the input/output orifices of each tube, etc. For instance, the device (e.g., the source 108 and regulator 110) may include an oxygen sensor that measures the output, which may be configured to electronically modify the flow rate of one or both tubes to ensure the output is suitable for achieving the desired oxygen partial pressure level.

Figure 2:
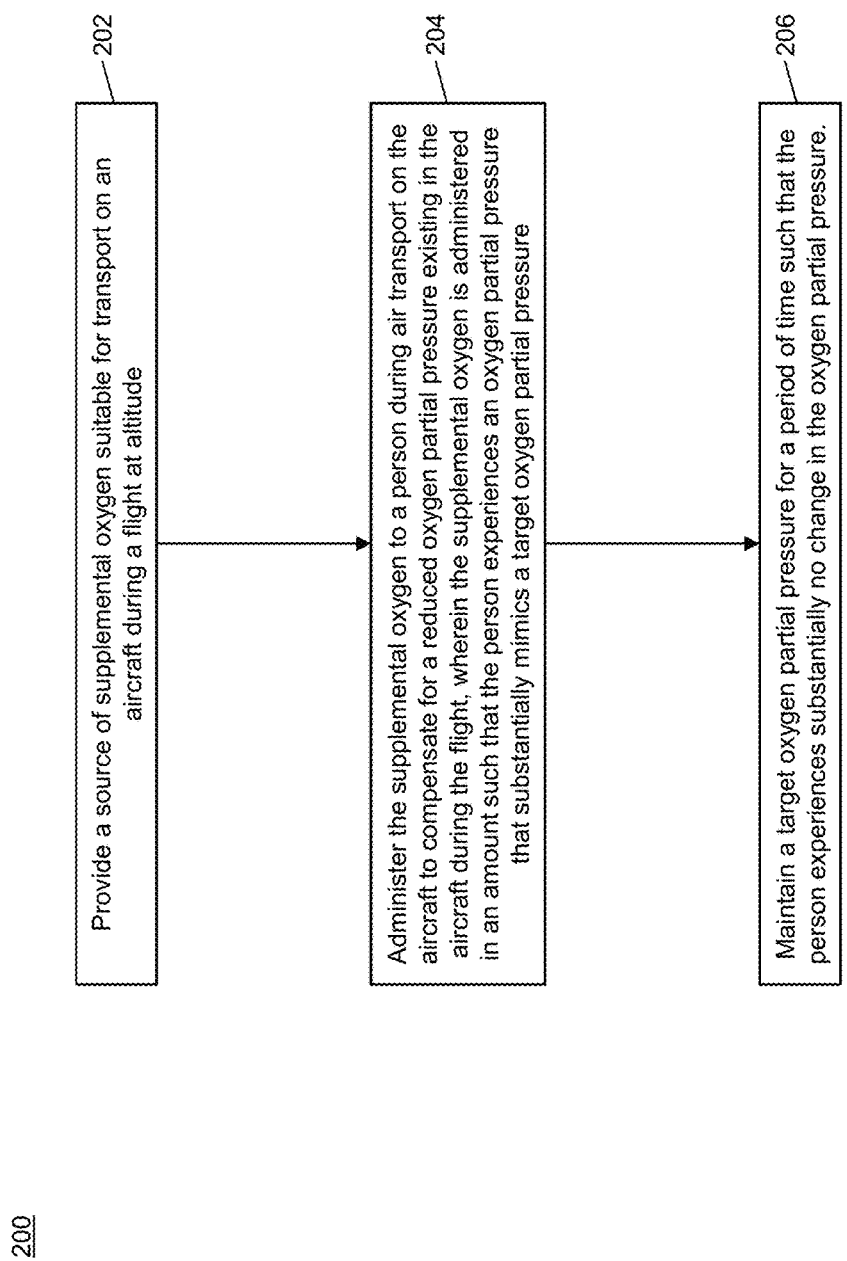
FIG. 2 is a flow chart illustrating an exemplary method for post-flight seizure prevention in accordance with exemplary embodiments.

In yet another embodiment, supplemental oxygen is administered as a preventative measure against the occurrence of one or more post-flight seizures. For instance, FIG. 2 illustrates a method 200 for the prevention of post-flight seizures via the use of supplemental oxygen. In step 202, a source 108 of supplemental oxygen that is suitable for transport on an aircraft during a flight at altitude, but is not particularly limited to any one specific device, is provided. In some embodiments, the source 108 of supplemental oxygen is a portable device. In other embodiments, it is preferable that the source 108 of the supplemental oxygen is not separately portable, but is instead mounted to or installed directly within the aircraft. In step 204, an amount of supplemental oxygen is administered to a person 102 during air transport on the aircraft to compensate for the reduced oxygen pressure existing in the aircraft during the flight. This amount of supplemental oxygen is set to provide a target oxygen partial pressure. Similar to that already discussed, the target oxygen partial pressure can be constant or adjustable. However, the target oxygen partial pressure is ideally set such that the individual receiving the supplemental oxygen experiences no change in the oxygen partial pressure from the departure airport to the arrival airport. In some embodiments, the method 200 may include step 206, where the target oxygen partial pressure may be maintained for a period of time such that the person 102 experiences substantially no change in the oxygen partial pressure.

The post-flight seizure prevention method may also involve the acquisition and return of the portable oxygen source 108. Particularly, the post-flight seizure prevention method may include the additional step of obtaining the portable source 108 of supplemental oxygen from a designated location in a departure airport prior to departure. The post-flight seizure prevention method may further include returning the portable source 108 of supplemental oxygen to a designated location in an arrival airport following landing.

In any of the embodiments described herein, the target oxygen partial pressure may be set as the oxygen partial pressure of an initial location 104, also referred to as a departure city, of the person 102 receiving the supplemental oxygen. Conversely, the target oxygen partial pressure may be set as the oxygen partial pressure of an end location 106, also referred to as an arrival city. The target oxygen partial pressure may also be set, in any of the described embodiments, to the oxygen partial pressure which corresponds to the location 104 where the person 102 receiving the supplemental oxygen is normally accustomed. This may the person's home city.

In any of the embodiments described herein, the target oxygen partial pressure may be constant or variable during the course of the administration of supplemental oxygen. When the target oxygen partial pressure is variable over the course of the administration, the variance can be effectuated by any manner known in the field.

In any of the disclosed embodiments, the administration of supplemental oxygen, whether it undercompensates or overcompensates for the reduced oxygen partial pressure environment is preferable to providing no compensation whatsoever. In this regard, the supplemental oxygen may be administered for the entire period of time when the individual 102 is exposed to reduced oxygen partial pressure. Alternatively, the supplemental oxygen may be administered for only a subset of the time period during which the person 102 is exposed to reduced oxygen partial pressure. Supplemental oxygen may be administered continuously or intermittently in any scenario.

The methods described herein seek to minimize or eliminate the delayed negative effects on a person's physiology resulting from exposure to reduced oxygen partial pressure for some period of time. Although directed to accommodate otherwise healthy individuals 102 who have special sensitivities to reduced oxygen partial pressure environments 106 and persons 102 having pre-existing neurological conditions, such as epilepsy, no individual 102 is exempt from seeking the benefit of the methods described herein. The administration of supplemental oxygen may, in addition to preventing the delayed effects of exposure to a reduced oxygen partial pressure environment 106 as described herein, be employed by a healthy person 102, for example, to facilitate work productivity, enhance concentration, or the like while at altitude.

Techniques consistent with the present disclosure provide, among other features, methods for minimizing the delayed effects of exposure to reduced oxygen partial pressure. While various exemplary embodiments of the disclosed system and method have been described above it should be understood that they have been presented for purposes of example only, not limitations. It is not exhaustive and does not limit the disclosure to the precise form disclosed. Modifications and variations are possible in light of the above teachings or may be acquired from practicing of the disclosure, without departing from the breadth or scope.

What is claimed is:

1. A post-flight seizure prevention method comprising:
    determining an initial target oxygen partial pressure for a first geographic location;
    determining an end target oxygen partial pressure for a second geographic location;
    providing a source of supplemental oxygen,
    setting said source of supplemental oxygen to said end target oxygen partial pressure, wherein said source of supplemental oxygen is suitable for transport on an aircraft during a flight at altitude; and
    administering said supplemental oxygen to a person during air transport on the aircraft to compensate for a reduced oxygen partial pressure existing in the aircraft during the flight,
    wherein said supplemental oxygen is administered in an amount such that the person experiences an oxygen partial pressure that substantially mimics said end target oxygen partial pressure, and
    wherein the person receiving the supplemental oxygen has a pre-existing neurological condition.

2. The post-flight seizure prevention method of claim 1, wherein the initial target oxygen partial pressure is the oxygen partial pressure of a departure city.

3. The post-flight seizure prevention method of claim 2, wherein the person is routinely accustomed to the oxygen partial pressure of the departure city.

4. The post-flight seizure prevention method of claim 1, wherein the end target oxygen partial pressure is the oxygen partial pressure at sea level.

5. The post-flight seizure prevention method of claim 1, further comprising:
    adjusting an oxygen partial pressure on said source of supplemental oxygen, automatically or manually, during the flight from said initial target oxygen partial pressure to said end target oxygen partial pressure based on one or more pressure sensors located on said source of supplemental oxygen.

6. The post-flight seizure prevention method of claim 5, wherein the oxygen partial pressure of a departure city is set as the initial target oxygen partial pressure and the oxygen partial pressure of an arrival city is set as the end target oxygen partial pressure.

7. The post-flight seizure prevention method of claim 1, further comprising:
obtaining said source of supplemental oxygen from a designated location in a departure airport prior to departure, the source of supplemental oxygen being a portable device.

8. The post-flight seizure prevention method of claim 7, further comprising:
returning the source of supplemental oxygen to a designated location in an arrival airport following landing.

9. The post-flight seizure prevention method of claim 1, wherein the supplemental oxygen is administered continuously such that the end target oxygen partial pressure is substantially maintained during the flight.

10. The post-flight seizure prevention method of claim 1, wherein said supplemental oxygen is administered for at least a portion of the flight.

11. The post-flight seizure prevention method of claim 1, wherein the pre-existing neurological condition is epilepsy.

12. A method for minimizing delayed effects of exposure to a reduced oxygen partial pressure comprising:
determining an initial target oxygen partial pressure for a first geographic location;
determining an end target oxygen partial pressure for a second geographic location;
providing a source of supplemental oxygen,
setting the source of supplemental oxygen to said initial target oxygen partial pressure, wherein said source of supplemental oxygen is suitable for transport on an aircraft during a flight at altitude;
administering the supplemental oxygen to a person during air transport on the aircraft to compensate for the reduced oxygen partial pressure existing in the aircraft during the flight; and
maintaining said initial target oxygen partial pressure for a period of time such that the person experiences substantially no change in oxygen partial pressure,
wherein said initial target oxygen partial pressure is an oxygen partial pressure to which the person is routinely accustomed or acclimatized, and
wherein the person receiving the supplemental oxygen has a pre-existing neurological condition.

13. The method for minimizing delayed effects of exposure to a reduced oxygen partial method of claim 12, further comprising:
adjusting an oxygen partial pressure on said source of supplemental oxygen, automatically or manually, during the flight from said initial target oxygen partial pressure to said end target oxygen partial pressure based on one or more pressure sensors located on said source of supplemental oxygen.

14. A method for minimizing delayed effects of exposure to a reduced oxygen partial pressure comprising:
determining an initial target oxygen partial pressure for a first geographic location;
determining an end target oxygen partial pressure for a second geographic location;
providing a source of supplemental oxygen;
setting said source of supplemental oxygen to said end target oxygen partial pressure, wherein, said source of supplemental oxygen is suitable for transport on an aircraft during a flight at altitude;
administering an amount of supplemental oxygen to a person exposed to the reduced oxygen partial pressure that substantially mimics said end target oxygen partial pressure at said second geographic location; and
maintaining the end target oxygen partial pressure for a period of time such that the person experiences substantially no change in oxygen partial pressure from said initial target oxygen partial pressure,
wherein the initial target oxygen partial pressure is an oxygen partial pressure to which the person is routinely accustomed or acclimatized.

15. A method for minimizing delayed effects of exposure to a reduced oxygen partial pressure comprising:
determining an initial target oxygen partial pressure for a first geographic location;
determining an end target oxygen partial pressure for a second geographic location;
providing a source of supplemental oxygen,
setting said source of supplemental oxygen to said end target oxygen partial pressure, wherein said source of supplemental oxygen is suitable for transport on an aircraft during a flight at altitude; and
administering an amount of supplemental oxygen to a person exposed to the reduced oxygen partial pressure that substantially mimics said end target oxygen partial pressure,
and
wherein the person receiving the supplemental oxygen is a person that does not have a pre-existing neurological condition.

16. The method of claim 15, wherein the administering of supplemental oxygen is for the purpose of facilitating work productivity and enhanced concentration at altitude for the person.

* * * * *